US009445623B2

(12) United States Patent
Wilkes et al.

(10) Patent No.: US 9,445,623 B2
(45) Date of Patent: Sep. 20, 2016

(54) NON-ALCOHOLIC WINE BEVERAGE

(76) Inventors: Donald F. Wilkes, Santa Monica, CA (US); Kelly Chavarrio, Montebello, CA (US)

( * ) Notice: Subject to any disclaimer, the term of this patent is extended or adjusted under 35 U.S.C. 154(b) by 721 days.

(21) Appl. No.: 12/433,390

(22) Filed: Apr. 30, 2009

(65) Prior Publication Data

US 2009/0297681 A1 Dec. 3, 2009

Related U.S. Application Data

(63) Continuation-in-part of application No. PCT/US2008/010457, filed on Sep. 8, 2008.

(60) Provisional application No. 60/935,944, filed on Sep. 7, 2007, provisional application No. 61/079,484, filed on Jul. 10, 2008.

(51) Int. Cl.

| C12H 3/00 | (2006.01) |
|---|---|
| A23L 2/52 | (2006.01) |
| A23L 1/30 | (2006.01) |
| A23L 2/02 | (2006.01) |
| A23L 2/38 | (2006.01) |
| A23L 2/40 | (2006.01) |
| A23L 2/54 | (2006.01) |
| A61K 36/82 | (2006.01) |
| A61K 36/87 | (2006.01) |

(52) U.S. Cl.
CPC ............... *A23L 2/52* (2013.01); *A23L 1/3002* (2013.01); *A23L 2/02* (2013.01); *A23L 2/38* (2013.01); *A23L 2/40* (2013.01); *A23L 2/54* (2013.01); *A61K 36/82* (2013.01); *A61K 36/87* (2013.01)

(58) Field of Classification Search
CPC .......... A23L 1/3002; A23L 2/02; A23L 2/38
USPC ............ 426/15, 590, 534, 477, 407, 592, 14
See application file for complete search history.

(56) References Cited

U.S. PATENT DOCUMENTS

| 4,775,538 A * | 10/1988 | Boucher ................. C12G 3/12 426/14 |
|---|---|---|
| 5,780,086 A | 7/1998 | Kirksey et al. |
| 6,099,854 A * | 8/2000 | Howard ................ A23L 1/3002 424/439 |
| 2004/0170730 A1* | 9/2004 | Rodney ..................... A23L 2/54 426/407 |
| 2006/0039972 A1 | 2/2006 | Aldritt et al. |
| 2006/0216392 A1 | 9/2006 | Tsutsuashvili |
| 2006/0287256 A1 | 12/2006 | Raederstorff et al. |
| 2007/0160734 A1 | 7/2007 | Van Bokkelen et al. |
| 2008/0199413 A1 | 8/2008 | Goralczyk et al. |
| 2008/0213433 A1 | 9/2008 | Feller et al. |
| 2009/0186119 A1* | 7/2009 | Draijer ..................... A23C 9/13 426/2 |

FOREIGN PATENT DOCUMENTS

| FR | 2 767 533 | 2/1999 |
|---|---|---|
| JP | 200667951 | * 3/2006 |
| WO | WO 03/099040 | 12/2003 |
| WO | WO-2009/032323 A1 | 3/2009 |

OTHER PUBLICATIONS

FR2767533, Derwent Abstract.*
JP200667951, Derwent Abstract.*
FR2767533, Derwent Abstract, Feb. 26, 1999.*
Meindi, Maximilian, "Refinement and Quality Preservation of Foodstuffs and Luxury Foods from Juice to Energy—and Wellness Foods," drink Technology + Marketing, IMATEC, Herrschling, Germany, Jun. 2007.
Storchmann, Karl, Resveratrol in Beer and "Fortified Wine," American Association of Wine Economists, Wine and Food Economics Blog, posted Nov. 29, 2008. http://wine-econ.org/2008/11/29/resveratrol-in-beer-and-fortified-wine.aspx.
Garret, Stuart, "Resveratrol-enhanced Red and White Wines Marketed by Global Beverage Innovations Under Label, Anti-Ageing Wine+Resveratrol," NewsBlaze, published Dec. 19, 2008. http://newsblaze.com/story/20081219125602000002.ew/topstory.html.
International Search Report and Written Opinion from PCT/US08/10457.
Resvida(TM)—Promotes Healthy Aging; DSM Presentation; downloaded 2008.
Supplementary European Search Report, 2008.

* cited by examiner

*Primary Examiner* — Helen F Heggestad
(74) *Attorney, Agent, or Firm* — Michael N. Cohen; Cohen IP Law Group PC

(57) ABSTRACT

A carbonated beverage prepared from dealcoholized wine base and having from about 150 mg to about 700 mgs of polyphenols per six to eight ounce serving. The beverage can contain from about 0.001 to about 0.01 percent resveratrol.

20 Claims, No Drawings

NON-ALCOHOLIC WINE BEVERAGE

CROSS REFERENCE TO RELATED APPLICATIONS

This application is a Continuation-in-Part of International Application No. PCT/US2008/010457, filed Sep. 8, 2008, which claims priority to U.S. Provisional Application Nos. 60/935,944, filed Sep. 7, 2007 and 61/079,484, filed Jul. 10, 2008, the specifications of which are hereby incorporated by reference in their entirety.

BACKGROUND OF THE INVENTION

1. Field of the Invention

The present invention relates generally to beverages, and more particularly to alcohol-free carbonated wine beverages.

2. Related Art

The consumption of non-alcoholic red wine is increasing worldwide, particularly in the United States, Europe and Asia. Consumers are demanding healthier and functional beverages for daily consumption. Red wine has intrinsic health benefits associated with polyphenol antioxidant grape compounds, and has been shown to improve heart health. However, there are consumption limitations on the drinking of wine, due to its alcohol content, when compared to traditional soft drinks. Even with the health benefits associated with moderate consumption of red wine and the wealth of research on the subject, many cardiologists don't suggest drinking larger amounts of red wine given the effects and risks associated with alcohol.

There is a need for a beverage that can offer the benefits of red wine without the disadvantages associated with the consumption of alcohol.

BRIEF SUMMARY OF THE INVENTION

The invention is an innovative, lightly carbonated and tunnel pasteurized beverage utilizing an alcohol-free wine base that has the same or more polyphenols per 6 to 12 oz serving than a glass of red wine. The invention provides the health benefits and taste of red wine without the alcohol in a refreshing and functional, lightly carbonated soft drink.

The invention provides the novel use of dealcoholized wine grape extractives obtained after prolonged fermentation. The invention can utilize red wine grape extractives, for example from a Cabernet, white wine extractives, for example from a Sauvignon Blanc, or mixtures thereof. In order to protect the wine base that has been stripped of a majority of alcohol from, for example, growth of Mycoderma Vini (vinegar bacteria and yeast) and loss of fruit flavor, a nitrogen "ullage" or oxidative rinse can be utilized to replace any air or dissolved oxygen that remains in the finished dealcoholized wine base. Process technology available from, for example, INMATEC (Herrsching, Germany) can be used for dosing with nitrogen. (See "Refinement and Quality Preservation of Foodstuffs and Luxury Foods From Juice to Energy- and Wellness Foods" by Maximiilan Meindi, IMATEC, Herrschling, Germany, drink TECHNOLOGY+MARKETING—June 2007.) The quantity of inert depends on the variety of grapes used in the fermentation and production of the wine. Generally, nitrogen is added in a quantity that is about 2.5-5 times the emptiness volume of the container. For example, a 10,000 liter tank filled to 80% has a 2,000 liter emptiness volume and would require minimum 2.5×2,000 liters, or about 5,000 liters nitrogen.

In some embodiments, the wine base contains a high concentration of polyphenol compounds, for example, red wine base can include high concentrations of polyphenols. If necessary, spray dried red wine flavonoids or polyphenols can be added, for example as a red wine concentrate powder, to increase the polyphenol or flavonoid content to a level corresponding to greater than 150 mg in a single serving. In other embodiments, green tea extractives or tea solids can be added as a source of polyphenol extractives. Antioxidant synergy can be obtained through the combination of high polyphenol containing juice concentrates of pomegranate and cherry; natural berry fruit flavors components, and natural wine essence. The formulation can utilize natural flavor modifiers and taste receptor astringency blockers, which modulate the undesirable taste defects of the high concentration of polyphenol compounds. The product can be processed with light carbonation and tunnel pasteurization requires only small amounts of added preservatives.

Further objectives and advantages, as well as the structure and function of preferred embodiments will become apparent from a consideration of the description and examples.

DETAILED DESCRIPTION OF THE INVENTION

Embodiments of the invention are discussed in detail below. In describing embodiments, specific terminology is employed for the sake of clarity. However, the invention is not intended to be limited to the specific terminology so selected. While specific exemplary embodiments are discussed, it should be understood that this is done for illustration purposes only. A person skilled in the relevant art will recognize that other components and configurations can be used without parting from the spirit and scope of the invention. All references cited herein are incorporated by reference as if each had been individually incorporated.

The terms "flavonoid" and "polyphenol" are used interchangeably herein. These terms are intended to refer to naturally occurring chemical substances found in plants, including grapes and other fruits, particularly in the skins, and are characterized by the presence of more than one phenol group per molecule. Polyphenols include, for example, tannins, and phenylpropanoids such as lignins and flavonoids. As used herein, the term polyphenol includes polyphenolic phytoalexin compounds such as resveratrol. Such compounds are alternatively referred to as polyphenol antioxidants, and have been shown to be important in combating oxidative stress that can contribute to the causation of some neurodegenerative and cardiovascular diseases. The health benefits of polyphenol antioxidants has been the subject of a growing body of health research in recent years. There is strong experimental evidence of their ability to affect the body's reaction to allergens, viruses, and carcinogens. They have shown anti-allergic, anti-inflammatory, anti-microbial and anti-cancer activity.

Generally, quantities described herein are expressed as amount per eight (8) ounce serving. However, the advantages of the invention can be obtained if the quantity described is present in any single serving size, for example from 6 to 12 ounces. Thus, any quantity described as being "per 8 oz serving" could be present in any single serving size from 6-12 ounces, for example 6 ounces, 8 ounces, 10 ounces, or 12 ounces.

The present invention is a unique ready to drink beverage product. Shelf life is increased by using tunnel pasteurization and, if necessary, a small amount of preservatives to ensure the wine flavors and wine concentrate maintain their flavor integrity. Velcorin® (from LANEXX, Pittsburgh, Pa.) can also be added as a processing aid. The use of Velcorin® may eliminate the need for added preservatives to the finished beverage. Other suitable preservation methods can also be used. Typically, wine has alcohol to act as a natural preservative, together with added sulfites. In order to achieve a shelf stable system, alcohol-free products embodying the present invention can utilize an innovative solution to address the microbiological stability issues in using wine extractives in a beverage without alcohol which may be fortified with red wine polyphenols or other wine extracts.

A product according to an exemplary embodiment of the present invention can be prepared from a dealcoholized red wine base. The red wine base is a red wine grape extractive, typically obtained from prolonged fermentation. The wine base can be prepared from, for example, Cabernet Sauvignon, Merlot, Pinot Noir, Claret, Sangiovese or other red wine varietals. Advantageously, the wine base is of a type that provides relatively high concentrations of polyphenol compounds. The wine base is dealcoholized, for example by the use of a Spinning Cone Column or other techniques, to contain not more than about 0.5% alcohol. In some embodiments, the wine base can contain red wine polyphenols in a sufficient quantity to provide over 100 mg of polyphenols, for example about 100 to 1000 mg of polyphenols or about 100-800 mg of polyphenols, per 8 oz. serving of the finished product. In some embodiments, the wine base can contain wine polyphenols in a sufficient quantity to provide over 150 mg, for example about 150 to 1000 mg of polyphenols or about 150-700 mg of polyphenols or about 150-500 mg of polyphenols, per 8 oz. serving of the finished product. If the desired amount of polyphenols can not be reached by use of the wine base alone, the polyphenol content can be increased by adding a secondary source of polyphenols. The secondary source of polyphenols can be, for example, spray dried red wine polyphenols such as a red wine concentrate powder, solid or liquid concentrates from other fruits containing polyphenols, tea extracts or other sources of polyphenols. Other extractives of high polyphenol juices include, for example pomegranate, blueberry, raspberry, blackberry, cranberry, mangosteen, acai and red grape juice concentrate.

In another exemplary embodiment, a product can be prepared from a dealcoholized white wine base, for example a Sauvignon Blanc. Additives that increase the polyphenol content or enhance the flavor can be used. For example, in some embodiments, a secondary source of polyphenols, for example tea extracts, can be added to increase the polyphenol concentration to levels recited above. Additives can include, for example, grape juices or juice concentrates, apple juices or juice concentrates and tea extracts, for example green tea extracts.

The combination of the wine base and, if necessary, added concentrate can provide a sufficient quantity of polyphenols to provide health benefits equivalent to one to two 6 to 8 oz serving of red wine. The wine base can comprise from about 25% to about 75% of the finished product, taking into account water added in the product. More particularly, the dealcoholized wine base can comprise from about 35% to about 65%, about 45% to about 55% or about 50% of the finished product. The amount of wine concentrate powder, tea extract or other source of additional polyphenols can be, for example, up to about 5%, up to about 2%, up to about 1%, or up to about 0.5% of the finished product.

Additional antioxidant benefits can be added by the use of high polyphenol containing juice concentrates. For example, pomegranate juice concentrate and/or cherry juice concentrates, such as sour cherry or sweet cherry juice concentrates, can also be added. Other juice concentrates include white grape juice concentrates and apple juice concentrates, for example Granny Smith apple juice concentrate. Such juice concentrates can be added for flavor enhancement as well as, in addition to, or instead of, being added to increase antioxidant content. One or more juice concentrates can be added, with each comprising an amount of up to about 13% of the finished product, up to about 10% of the finished product, or up to about 5% of the finished product. In some embodiments, juice concentrates can be added such that the total amount of juice concentrate is up to about 10% of the finished product, up to about 5% of the finished product, from about 2% to about 5% or from about 2% to about 3% of the finished product.

In exemplary embodiments of the invention, resveratrol can be added to the composition. In exemplary embodiments, resveratrol is added in amount of about 0.001% to about 0.01% (w/w) of the composition. Resverstrol, 3,5,4'-trihydroxystilbene or 5-(4-hydroxystyryl)benzene-1,3-diol, is a polyphenolic phytoalexin compound found largely in the skins of red grapes, and has become commercially available, for example as Resvida™ (from DSM Nutritional Products, Inc.) In exemplary embodiments, the resveratrol is exclusively or predominantly the trans- or (E)-isomer. Resveratrol has been postulated or shown to provide numerous health benefits, many of which are common with other polyphenols. For example, resveratrol is a potent antioxidant that helps prevent free radical damage and reduce oxidative stress that can lead to premature aging of cells. Resveratrol helps support the body's natural defense mechanism and promotes mitochondrial biogenesis and function. Resveratrol has been found to mimic the effect of calorie restricted diets and its antioxidant activity also supports cardiovascular health. Reservatrol may be present as a distinct compound or may be present in a complexed or conjugated form. One alternative form is the 3-β-glucoside form, 2-[3-hydroxy-5-[(E)-2-(4-hydroxyphenyl)ethenyl]phenoxy]-6-(hydroxymethyl)-oxane-3,4,5-triol, also known as polydatin or piceid. Resveratrol also helps to promote sustained muscle function and helps to reduce muscle fatigue.

An efficacious amount of reseveratrol can be about 30 mg to 150 mg per day. Exemplary compositions according to the present invention can include up to about 45-50 mg resveratrol per 8 fluid ounces of the composition. In exemplary embodiments, the composition can include up to about 25 mg resveratrol per 8 fluid ounces; up to about 12.5 mg resveratrol per 8 fluid ounces, up to about 6.25 mg resveratrol per 8 fluid ounces or about 3.35 mg resveratrol per 8 fluid ounces. Exemplary embodiments of the invention can contain from about 3.35 mg to about 45 mg resveratrol per 8 fluid ounces; from about 3.35 mg to about 25 mg resveratrol per 8 fluid ounces; from about 3.35 mg to about 12.5 mg resveratrol per 8 fluid ounces; from about 3.35 mg to about 6.25 mg resveratrol per 8 fluid ounces; or more than about 3.35 mg resveratrol per 8 fluid ounces. Other amounts of reseveratrol can be used. Resveratrol can be used with other ingredients that contain other polyphenols or with other polyphenol additives; for the dealcoholized wine base, and other natural juices that are sources of polyphenols.

In exemplary embodiments, resveratrol may be added in an amount up to about 100 g per 100 gallons of prepared composition. In an exemplary embodiment, resveratrol is added at a rate of up to about 50 g per 100 gallons of solution. In some embodiments, the amount of resveratrol is about more than about 5 g per 100 gallons of the composition. Exemplary embodiments of the invention can include, for example, from about 5 g to about 40 g of resveratrol per 100 gallon batch; from about 5 g to about 20 g of resveratrol per 100 gallon batch; from about 5 g pounds to about 10 g of resveratrol per 100 gallon batch or about 5.36 g per 100 gallon batch. Exemplary amounts of reservatrol used in a 100 gallon batch are 5.35 g, 10 g, 20 g, and 40 g.

The Brix range of the juice concentrates used will depend on the particular concentrate and the quantity used. Typical Brix ranges can be from about 40° Bx to about 80° Bx. Examples of specific concentrates and Brix ranges include sour cherry juice concentrate with a brix range of about 40-68° Bx, dark sweet cherry juice concentrate with a brix range of about 40-68° Bx, pomegranate juice concentrate with a Brix range of about 40-66° Bx, white grape juice concentrate with a Brix range of about 60-75° Bx, and apple juice concentrate with a Brix range of about 65-80° Bx. These juice concentrates and Brix ranges are provided only by way of example and are not intended to limit the composition to any particular, specific product. Additionally, other components can be used to enhance the polyphenol content, such as green tea extracts, for example.

Additional antioxidants that can act as a "cocktail" delivery system, can also be added to the composition. These antioxidants can be natural or synthetic compounds. Non-limiting examples of antioxidants include COQ10, vitamin E and derivatives thereof, de-fatted Acai, and berry extract blends, including blends that contain Acai. Other sources of antioxidants include green teas, black teas, grape, cranberry, black currant, elderberry, strawberry, bilberry, mangosteen, and raspberry. These sources can be added as, for example, liquid or solid fruit, juices, juice concentrates and extracts and or their concentrated polyphenol compounds.

A blend of sodium benzoate and potassium sorbate can be used in order to avoid oxidation of the wine and to insure the stability of the finished beverage over its shelf life, i.e. manufacture, distribution, and store and consumer shelf time. The amount of sodium benzoate and potassium sorbate can be less than about 0.05% or about 0.025% of the final product to about 500 PPM each. Alternatively or in addition, benzoic acid or other salts thereof and/or sorbic acid and other salts thereof can be added as preservatives. Another preservation technique would be the use of Velcorin®, added as a processing aid. The use of Velcorin may eliminate the need for added preservatives to the finished beverage.

Typically, wine contains alcohol to act as a natural preservative, and frequently has added sulfites. In order to achieve a shelf stable system, the present invention can utilize an innovative solution to address the microbiological stability issues in using wine extractives in a beverage without alcohol. The product can be carbonated to about 1.5 to about 4.0 volumes or about 2.5 to about 3.0 volumes. Exemplary embodiments can be carbonated with about 2.8 volumes $CO_2$. The product can also be tunnel pasteurized to help preserve the quality and extend shelf life. In an exemplary embodiment, the product is tunnel pasteurized at about 160° F. (about 71° C.) for about 10 minutes, although other times and temperatures can be used as is known in the art and as necessary to achieve sufficient preservative effect. In addition, a nitrogen flush can be added prior to capping the finished drink to eliminate any remaining oxygen in the container head space. These processes prevent further fermentation of the wine base and make the product shelf stable. The carbonation and/or nitrogen flush can help create an "anaerobic" environment which minimizes oxidative degradation. In addition, carbonation has the benefit of providing a unique taste sensation that mimics alcohol's drying effect.

Flavor modifiers and taste receptor astringency blockers can be added to modulate the undesirable taste effects that might result from the high content of polyphenol compounds. Examples include B-Blocker™ and/or Zatiate™, which are available from Blue Pacific Flavors of Industry, Calif. B-Blocker™ utilizes GRAS approved ingredients that can successfully block one or more of the 25 bitter taste receptors of the tongue. Zatiate™ utilizes GRAS approved ingredients with other natural flavors as a mouth watering agent to modify astringency from complex acids and or polyphenol juice extractives. Other suitable flavor modifiers and taste receptor astringency blockers can be added and their specific identities and use will be known to persons skilled in the art. Flavor modifiers and taste receptor astringency blockers of this type can each be added in amounts of up to about 0.10%, for example from about 0.05% to about 0.10% of the finished product, or the total amount of flavor modifiers and taste receptor astringency blocker can comprise up to about 0.10%, or example from about 0.05% to about 0.10% of the finished product. The addition of flavor modifiers and astringency blockers enhances drinkability by providing "gulp ability" and satiation even at the high levels of polyphenol fortification present in the beverage.

The beverage can be unsweetened or can be sweetened with, for example, from 0 to about 10% sugar. Other natural or synthetic sweeteners can be added to achieve a similar taste. Examples of sweeteners include erythritol, sucralose, acesulfame potassium, aspartame, crystalline fructose, and agave nectar.

As will be known to persons skilled in the art, additional ingredients can be added to achieve the desired flavor, "mouthfeel," and shelf life stability. For example additional natural and artificial flavors and flavor blends can be added. Tartaric acid or its salts can also be added. Components such as citric acid and malic acid can be added for flavor modification and shelf-life stability. Citric and malic acid or their salts can be added in individual or combined amounts of up to about 0.1%, up to about 0.05%, or up to about 0.025%. Water is typically added to the composition in a range of from about 25% to about 75% of the finished product, in particular from about 30% to about 50% or about 40% of the finished product. In some embodiments, the finished beverage can have a final Brix value of about 10-15° Bx, for example, 11-12.5° Bx or about 11.9° Bx. In other embodiments, the finished beverage can have a final Brix value of about 5-10° Bx, for example, 6.5-8.5° Bx or about 7.9° Bx. The pH can be from about 2.5 to about 4.5, about 3.0 to about 4.0, or about 3.25 to about 3.50. The specific gravity of the finished composition can be from about 1.00 to about 1.10 or about 1.02 to about 1.05. Furthermore, although various components described herein are used for particular purposes, the ingredients and uses are exemplary and components may serve one or more functions and alternative ingredients that serve a desired function but are not specifically mentioned in this specification may be substituted.

In an exemplary embodiment of manufacturing a beverage according to the invention, the ingredients, including water, are combined. The composition in chilled and then carbonated to the desired $CO_2$ volumes, using methods known in the art. The product is then bottled into the appropriate package and tunnel pasteurized at 160° F. for about 10 minutes.

EXAMPLE 1

An exemplary Cabernet Soda composition according to the invention was prepared in a 100 gallon quantity by combining:

| Item | Quantity (lbs.) | Percentage |
| --- | --- | --- |
| Water Q.S. to 100 Gal. (Approx.) | 348.45 | 40.14 |
| Wine Dealcoholized Cabernet | 434.07 | 50.00 |
| Potassium Benzoate | 0.22 | 0.03 |
| Potassium Sorbate | 0.22 | 0.03 |
| Sugar | 52.09 | 6.00 |
| Sour Cherry Juice Conc. | 7.14 | 0.82 |
| Dark Sweet Cherry Juice Conc. | 10.22 | 1.18 |
| Pomegranate Juice Conc. | 8.55 | 0.98 |
| Citric Acid | 0.33 | 0.04 |
| Malic Acid | 0.33 | 0.04 |
| Red Wine Concentrate Powder | 2.08 | 0.24 |
| Fruit Flavor Pack Nat With Other Natural Flavors | 2.71 | 0.31 |
| Mouthfeel Solution | 0.87 | 0.10 |
| B-Blocker ™ Nat Flavor Modifier | 0.43 | 0.05 |
| Zatiate ™ Natural | 0.43 | 0.05 |

The ingredients were batched and chilled, followed by carbonating to about 2.8 volumes $CO_2$. The product was bottled and pasteurized at 160° F. for about 10 minutes. The finished drink of this formulation contained about 12% juice and had a Brix value of 11.92° Bx±0.5; a pH of about 3.47±0.1 and a specific gravity of about 1.0403±0.01.

EXAMPLE 2

An exemplary Sauvignon Blanc composition according to the invention was prepared in a 100 gallon quantity by combining:

| Item | Quantity (lbs.) | Percentage |
| --- | --- | --- |
| Water Q.S. to 100 Gal. (Approx.) | 367.03 | 42.751% |
| Wine Dealcoholized Sauvignon Blanc | 429.27 | 50.000% |
| Potassium Benzoate | 0.21 | 0.025% |
| Potassium Sorbate | 0.21 | 0.025% |
| Sugar | 40.78 | 4.750% |
| White Grape Juice Conc. (68° Bx) | 10.96 | 1.277% |
| Granny Smith Apple Juice Conc. (72° Bx) | 6.85 | 0.798% |
| Citric Acid | 0.43 | 0.050% |
| Malic Acid | 0.21 | 0.025% |
| Teavigo Green Tea Extract | 0.26 | 0.030% |
| Fruit Flavor Pack Nat Wonf | 1.03 | 0.120% |
| Mouthfeel Solution | 0.86 | 0.100% |
| B-Blocker ™ Natural Flavor Modifier | 0.43 | 0.050% |

The finished drink of this formulation contained about 12% juice and had a Brix value of 7.86° Bx±0.5; a pH of about 3.27±0.1 and a specific gravity of about 1.0288+0.01.

EXAMPLE 3

An exemplary Cabarnet composition according to the invention was prepared in a 100 gallon quantity by combining:

| Item | Quantity (lbs.) | Percentage |
| --- | --- | --- |
| Water Q.S. to 100 Gal. (Approx.) | 373.79 | 43.12% |
| Wine Dealcoholized Cabernet | 433.36 | 50.00% |
| Potassium Benzoate | 0.22 | 0.03% |
| Potassium Sorbate | 0.22 | 0.03% |
| Sugar Powder | 26 | 3.00% |
| RA97 Stevia Extract PWD844 | 0.08 | 0.01% |
| Sour Cherry Juice Conc. 68 Brix | 7.13 | 0.82% |
| Dark Sweet Cherry Juice Conc. 68 Brix | 10.2 | 1.18% |
| Pomegranate Juice Conc. 65 Brix | 8.53 | 0.98% |
| Citric Acid Powder | 0.33 | 0.04% |
| Malic Acid Powder | 0.33 | 0.04% |
| Red Wine Concentrate Powder | 2.08 | 0.24% |
| Resveratrol Resvida TG | 0.1 | 0.01% |
| Fruit Flavor Pack Natural | 1.84 | 0.21% |
| Synature Beverage Enhancer | 0.87 | 0.10% |
| Mouthfeel Solution | 0.87 | 0.10% |
| B-Blocker™ Nat Flavor Modifier | 0.43 | 0.05% |
| Zatiate™ Natural | 0.43 | 0.05% |

The finished drink of this formulation contained about 12% juice and had a Brix value of 7.00° Bx±0.5; a pH of about 3.56±0.1 and a specific gravity of about 1.0386+0.01.

EXAMPLE 4

Another exemplary Sauvignon Blanc composition according to the invention was prepared in a 100 gallon quantity by combining:

| Item | Quantity (lbs.) | Percentage |
| --- | --- | --- |
| Water Q.S. to 100 Gal. (Approx.) | 383.89 | 45.11% |
| Wine Dealcoholized Sauvignon Blanc | 425.43 | 49.99% |
| Potassium Benzoate | 0.21 | 0.02% |
| Potassium Sorbate | 0.21 | 0.02% |
| Sugar Powder | 20.21 | 2.37% |
| RA97 Stevia Extract | 0.06 | 0.01% |
| White Grape Juice Conc. 68 Brix | 10.86 | 1.28% |
| Granny Smith Apple Juice Conc. 72 Brix | 6.79 | 0.80% |
| Citric Acid Powder | 0.43 | 0.05% |
| Malic Acid Powder | 0.21 | 0.02% |
| Teavigo Green Tea Extract | 0.26 | 0.03% |
| Resveratrol Resvida TG | 0.1 | 0.01% |
| White Wine Flavor Pack | 0.17 | 0.02% |
| Synature Beverage Enhancer | 0.85 | 0.10% |
| Mouthfeel Solution | 0.85 | 0.10% |
| B-Blocker™ Nat Flavor Modifier | 0.43 | 0.05% |

The finished drink of this formulation had a Brix value of 3.5° Bx±0.5; a pH of about 3.55±0.1 and a specific gravity of about 1.0196+0.01.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A non-alcoholic wine beverage comprising a dealcoholized wine base and greater than about 150 mg polyphenols per 8 oz. serving, wherein said beverage contains sugar, a 1.6% to 5% juice concentrate, red wine concentrate powder, water, and is optionally carbonated.

2. A process for preparing non-alcoholic wine beverage comprising:
(1) mixing
(a) dealcoholized wine base comprising dealcoholized red wine extract-in an amount of from about 45% to about 55%;
(b) 0-10% sugar;
(c) from about 2% to about 5% of juice concentrate selected from the group consisting of sour cherry juice concentrate, sweet cherry juice concentrate, pomegranate juice concentrate, and combinations thereof;
(d) up to about 0.5% red wine concentrate powder; and
(e) water; and
(2) carbonating the liquid mixture;
wherein the beverage comprises greater than about 150 mg polyphenols per 8 oz. serving in the beverage; and from about 45% to about 55% of the liquid dealcoholized wine base.

3. The method of claim 2, wherein mixing further comprises adding polyphenols comprising resveratrol.

4. The method of claim 2, wherein the beverage comprises from about 0.001% (w/w) to about 0.1% (w/w) resveratrol.

5. The method of claim 2, wherein carbonating comprises carbonation at about 2.8 volumes of $CO_2$.

6. The method of claim 2, further comprising tunnel pasteurizing the liquid mixture.

7. The method of claim 6, wherein the tunnel pasteurizing comprises pasteurizing at about 160° F. for about 10 minutes.

8. The method of claim 2, wherein mixing further comprises adding one or more components selected from the group consisting of concentrate of pomegranate, flavor modifiers, taste receptor astringency blockers, spray dried red wine polyphenols, resveratrol, green tea extract, white grape juice concentrate and apple juice concentrate.

9. The method of claim 2, wherein mixing further comprises adding one or more components selected from the group consisting of natural berry fruit flavors components, natural wine essence, and fruit juice.

10. The method of claim 2, wherein the composition further comprising about 150 mg to about 700 mg polyphenols per 8 oz. serving.

11. The method of claim 2, wherein the composition further from about 5 mg to about 40 mg resveratrol per 8 oz. serving.

12. A process for preparing non-alcoholic wine beverage comprising:
(1) mixing
(a) [a liquid] dealcoholized wine base comprising dealcoholized white wine extract in an amount of from about 45% to about 55%;
(b) 0-10% sugar;
(c) from about 2% to about 5% of juice concentrate selected from the group consisting of white grape juice concentrate, apple juice concentrate and combinations thereof;
(d) up to about 0.5% green tea extract; and
(e) water; and
(2) carbonating the liquid mixture;
wherein the beverage comprises greater than about 150 mg polyphenols per 8 oz. serving in the beverage; and from about 45% to about 55% of the liquid dealcoholized wine base.

13. The method of claim 12, wherein mixing further comprises adding said polyphenols which comprise resveratrol.

14. The method of claim 13, wherein the beverage comprises from about 0.001% (w/w) to about 0.1% (w/w) resveratrol.

15. The method of claim 12, wherein carbonating comprises carbonation at about 2.8 volumes of $CO_2$.

16. The method of claim 12, further comprising tunnel pasteurizing the liquid mixture.

17. The method of claim 16, wherein the tunnel pasteurizing comprises pasteurizing at about 160° F. for about 10 minutes.

18. The method of claim 12, wherein mixing further comprises adding at least one component selected from the group consisting of concentrate of pomegranate, concentrate of cherry, flavor modifiers, taste receptor astringency blockers, spray dried red wine polyphenols, resveratrol, green tea extract, white grape juice concentrate apple juice concentrate.

19. The method of claim 12, wherein mixing further comprises adding at least one component selected from the group consisting of natural berry fruit flavors components, natural wine essence, and fruit juice.

20. The method of claim 12, wherein at least one of (c) or (d) is present in an amount to provide from about 5 mg to about 40 mg resveratrol per 8 oz. serving.

* * * * *